United States Patent [19]
Janke et al.

[11] 3,983,863
[45] Oct. 5, 1976

[54] HEART SUPPORT FOR CORONARY ARTERY SURGERY

[75] Inventors: Walter H. Janke, Fort Lauderdale, Fla.; Milford Barron, Grand Blanc, Mich.

[73] Assignee: American Hospital Supply Corporation, Evanston, Ill.

[22] Filed: June 2, 1975

[21] Appl. No.: 583,043

[52] U.S. Cl. .......................... 128/1 R; 128/303 R; 128/334 R
[51] Int. Cl.² ........................................ A61B 19/00
[58] Field of Search ............ 128/1 R, 132 R, 132 D, 128/155, 334 R, 335, 335.5, 303 R

[56] References Cited
UNITED STATES PATENTS

| 2,143,910 | 1/1939 | Didusch | 128/335.5 |
| 2,671,444 | 3/1954 | Pease | 128/334 R |
| 3,054,406 | 9/1962 | Usher | 128/334 R |
| 3,124,136 | 3/1964 | Usher | 128/334 R |

OTHER PUBLICATIONS

DeMeules et al. — Annals of Thoracic Surgery — vol. 16, No. 2, Aug. 1973, pp. 199–200.

*Primary Examiner*—Dalton L. Truluck
*Attorney, Agent, or Firm*—Lee R. Schermerhorn

[57] ABSTRACT

The heart support is formed of flat cloth tapes crossing each other at right angles and stitched together to provide a mesh with square openings. The support is heart shaped in outline with a transverse fixation tape having free ends extending laterally in opposite directions from the apex to secure the support to the heart of the patient. Each tape in the mesh is formed of a folded bias weave cloth capable of stretching to conform the support to the shape of the heart.

6 Claims, 3 Drawing Figures

U.S. Patent  Oct. 5, 1976  3,983,863
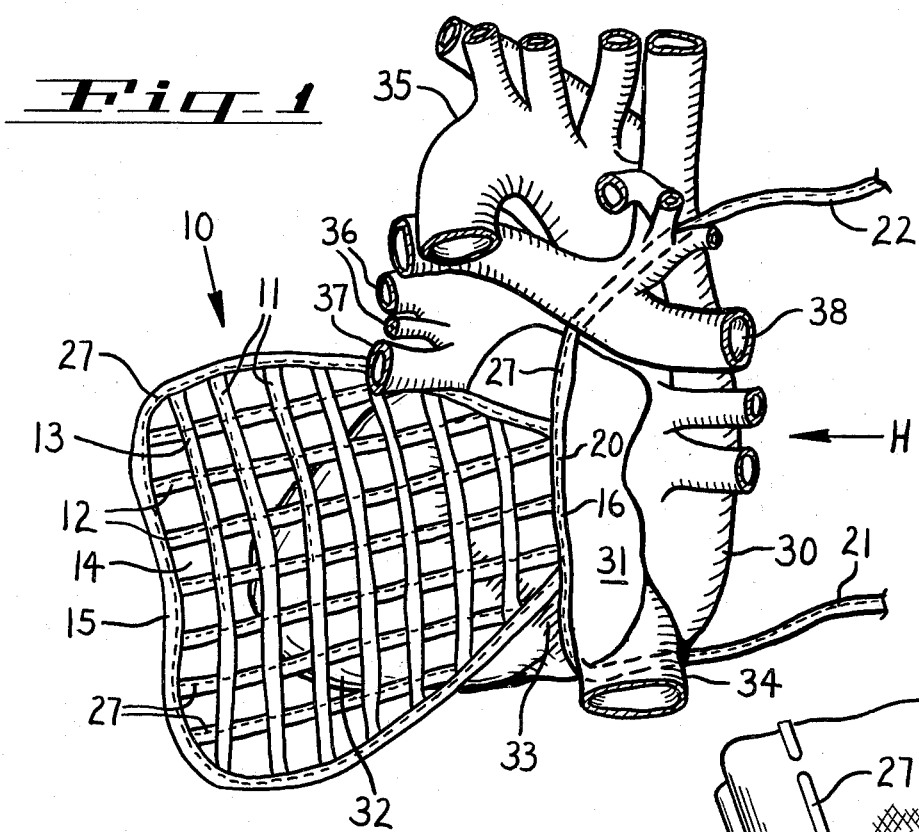
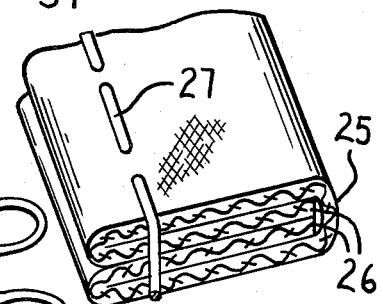
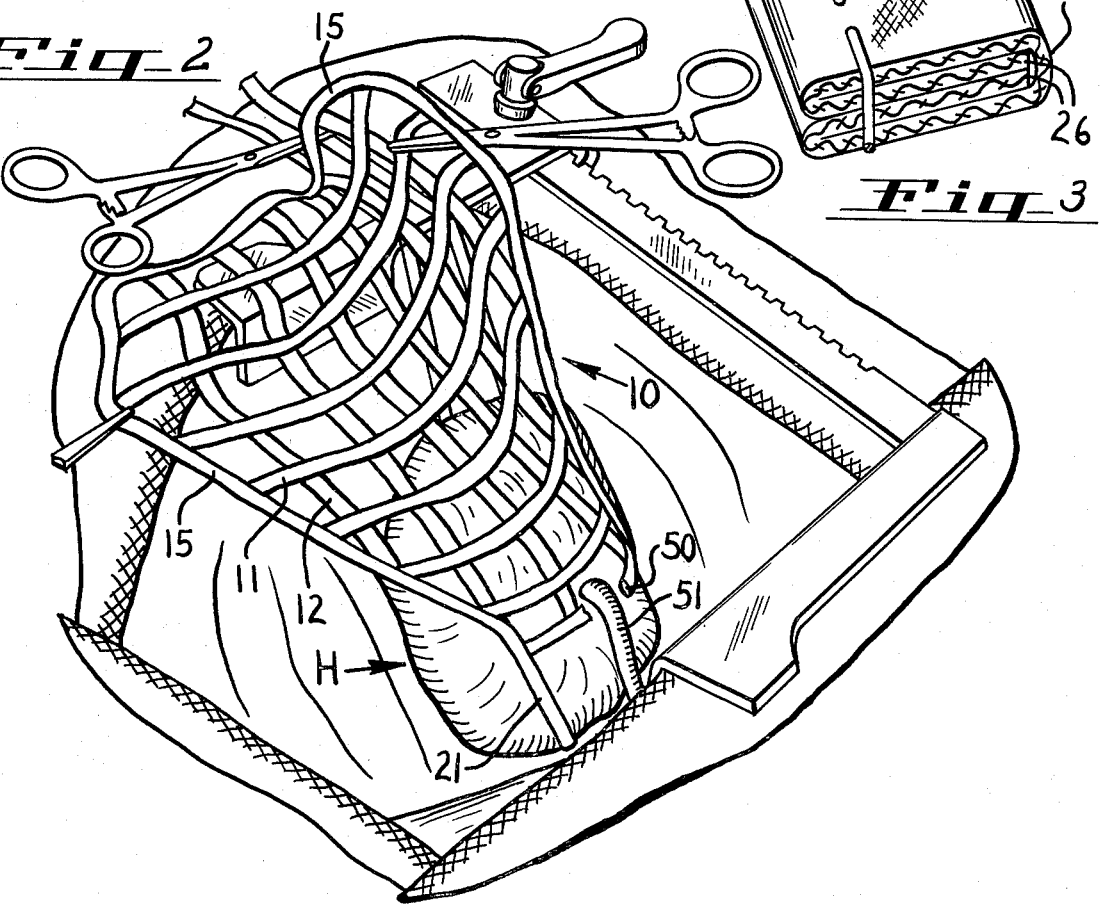

HEART SUPPORT FOR CORONARY ARTERY SURGERY

BACKGROUND OF THE INVENTION

This invention relates to a heart support for coronary artery surgery.

Bypass operations on the circumflex artery system are especially difficult because of the inaccessability of the field of operation on the posterior side of the heart. The conventional procedure is to have an assistant lift and rotate the heart about the axis of the inferior vena cava and the superior pulmonary veins. This is not only cumbersome but extremely tiring for both the assistant and the surgeon. The assistant does not have a view of the field of the operation and it is difficult to keep the heart in a steady position.

A fishnet support of rectangular outline has heretofore been proposed, but this is found to be unsatisfactory. The strands of a fishnet are extremely fine and inelastic causing them to impinge on the coronary arteries so as to stop all coronary circulation and possibly cause some additional myocardial damage.

Objects of the present invention are, therefor, to provide an improved heart support for coronary artery surgery, to provide a heart support which does not constrict the coronary circulation or cause other myocardial damage, and to provide a heart support constructed of cloth tapes of substantial width which are soft and stretchable to conform to the shape of the heart.

SUMMARY OF THE INVENTION

The present heart support is formed of flat cloth tapes crossing each other at right angles and stitched together to provide a mesh with square openings. The support is heart shaped in outline with a transverse fixation tape having free ends extending laterally in opposite directions from the apex to secure the support to the heart of the patient. Each tape in the mesh is preferably formed of a folded bias weave cloth capable of stretching to conform the support to the shape of the heart.

Thus, the tapes provide broad, soft and resilient surfaces in contact with the heart which do not restrict coronary circulation or cause other myocardial damage. Each tape is preferably folded from a wider strip of material so as to contain several thicknesses of the material.

The invention will be better understood and additional objects and advantages will become apparent from the following description of the preferred embodiment illustrated on the accompanying drawing. Various changes may be made in the details of construction and arrangement of parts and certain features may be used without others. All such modifications within the scope of the appended claims are included in the invention.

BRIEF DESCRIPTION OF THE DRAWING

FIG. 1 is a view of the posterior side of a heart showing the first step in the placement of the present heart support;

FIG. 2 is a view from above, on the operating table, showing the support in use; and FIG. 3 is a fragmentary view showing the construction of the tapes.

DESCRIPTION OF THE PREFERRED EMBODIMENT

The support 10 comprises a series of parallel tapes 11 crossing another series of parallel tapes 12 at points 13 where the tapes are stitched together to form a mesh having openings 14. The tapes 12 preferably extend perpendicular to the direction of tapes 11 and have the same spacing so as to form square openings at 14. The holder is heart shaped in outline, having a marginal tape 15 stitched to the ends of the tapes 11 and 12. The apex of the heart shaped outline is indicated at 16 where a fixation tape 20 is stitched to the tapes 12 and 15 and has free end portions 21 and 22 extending laterally in opposite directions from the apex 16.

Each tape 11, 12 and 20 is preferably formed from a strip of bias weave cotton cloth making the tape soft and stretchable. By way of example, as shown in FIG. 3, the strip of cloth has a longitudinal center fold 25 and the opposite edges 26 of the strip are folded inward toward the fold 25 to make a tape having a quadruple thickness of cloth.

In the case of tapes 12, 15 and 20, the four thicknesses of cloth are stitched together by a longitudinal line of stitching 27. Stitching 27 in the tapes 12 may also serve to secure tapes 11 and 12 together at the crossing points 13. Tapes 11 then need not contain the stitching 27 as they will be securely held in folded position by the stitching 27 in tapes 12 at closely spaced intervals. Other folding and stitching arrangements may be also used to form suitable tapes having multiple cloth thickness.

Marginal tape 15 has its fold 25 on the periphery of the holder and the ends of tapes 11 and 12 are inserted between the inturned edge portions 26 of the material of tape 15 and secured by the stitching 27 in tape 15. Thus, stitching 27 is applied to tapes 12 after these tapes are assembled on tapes 11 and then marginal tape 15 is assembled on the ends of tapes 11 and 12 and stitching 27 is applied to tape 15. In a similar manner the ends of tapes 12 and 15 are inserted between the inturned edge portions 26 of the material of tape 20 and secured by stitching 27 in tape 20.

FIG. 1 is a posterior view of a heart H, this being the underside when a patient is lying on his back on an operating table. In this posterior aspect a portion of the right atrium 30 is visible, most of the left atrium 31 is visible and a considerable portion of the left ventricle 32 is visible. The atrio-ventricular groove 33 separates the left atrium from the left ventricle. Also clearly in view are the inferior vena cava 34, the aortic arch 35, the upper left pulmonary veins 36, the lower left pulmonary vein 37 and the right pulmonary artery 38.

In using the heart support the apex of the left ventricle is lifted from the pericardial cavity and the support is placed around the posterior aspect of the atrio-ventricular groove 33 as shown in FIG. 1. The heart is then lowered into the pericardial cavity and the free end 21 of fixation tape 20 is pulled under the inferior vena cava 34. End 22 is pulled through the transverse sinus under the aorta and pulmonary artery 38. By pulling on the ends 21 and 22 the broad portion of the heart support remote from apex 16 is positioned snugly against the left atrium. The ends 21 and 22 are then tied or clamped together.

The broad end of support 10 is then pulled upward as shown in FIG. 2 exposing the circumflex artery system. By clamping the broad end of support 10 to the surgical drapes overlying the patient an obstructed view of the entire posteror heart surface is obtained. If any of the tapes in the mesh are in the way of surgery they can be cut out and the support will still be strong enough to hold the heart in the position described. For example, in FIG. 2 a tape has been cut at 50 to clear the circumflex coronary artery 51.

Thus, the present support holds the heart in steady position for bypass operations on the circumflex artery system and frees the assistant for other useful duties to aid the surgeon.

What is claimed is:

1. A heart support comprising a mesh of flat cloth tapes crossing each other at intervals to provide openings between said tapes, a marginal tape around the periphery of said mesh imparting a heart shaped outline to the support, said crossing tapes being stitched together at their crossing points and said marginal tape being stitched to the ends of said crossing tapes, and a fixation tape stitched to said crossing and marginal tapes at the apex of said heart shaped outline and having free ends extending laterally in opposite directions from said apex, said tapes being formed of bias weave material so as to be stretchable.

2. A heart support as defined in claim 1, said tapes being formed from strips of material folded longitudinally to multiple thickness.

3. A heart support as defined in claim 2, the ends of said crossing tapes being inserted in said fold of said marginal tape.

4. A heart support as defined in claim 2, said material having a middle fold and the edge portions being folded inward to provide quadruple thickness of material.

5. A heart support as defined in claim 4, said strips of material being approximately 2.5 cm wide, said tapes being approximately 6 mm wide, and said openings being approximately 1.5 cm on each side.

6. A heart support as defined in claim 2 including longitudinal stitching in certain of said tapes holding said material in folded condition and securing the tapes to each other at said crossing points.

* * * * *